United States Patent
Li et al.

(10) Patent No.: US 8,022,037 B2
(45) Date of Patent: Sep. 20, 2011

(54) SKIN WOUND HEALING COMPOSITIONS AND METHODS OF USE THEREOF

(75) Inventors: Wei Li, Altadena, CA (US); Mei Chen, Altadena, CA (US); David T. Woodley, Altadena, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/522,446

(22) PCT Filed: Jan. 8, 2008

(86) PCT No.: PCT/US2008/050520
§ 371 (c)(1),
(2), (4) Date: Jul. 8, 2009

(87) PCT Pub. No.: WO2008/086358
PCT Pub. Date: Jul. 17, 2008

(65) Prior Publication Data
US 2010/0035815 A1  Feb. 11, 2010

Related U.S. Application Data

(60) Provisional application No. 60/879,150, filed on Jan. 8, 2007.

(51) Int. Cl.
*A61K 38/00* (2006.01)
*A61K 45/00* (2006.01)
(52) U.S. Cl. ..................... 514/16.5; 424/85.2
(58) Field of Classification Search .......... None
See application file for complete search history.

(56) References Cited

U.S. PATENT DOCUMENTS

| 5,599,788 A | 2/1997 | Purchio et al. |
| 6,475,490 B1 * | 11/2002 | Srivastava et al. ......... 424/193.1 |
| 7,081,240 B1 | 7/2006 | Akella et al. |
| 2001/0034042 A1 * | 10/2001 | Srivastava .................... 435/68.1 |

OTHER PUBLICATIONS

Nemoto T. et al. Oligomeric forms of the 90-kDa heat shock protein. *Biochem J.* 1998. vol. 330, pp. 989-995.
International Search Report and Written Opinion of the International Searching Authority for PCT Application No. PCT/US08/50520, mailed May 8, 2008.
Cheng, C.F. et al. Transforming Growth Factor alpha (TGFalpha)-Stimulated Secretion of HSP90alpha: Using the Receptor LRP-1/CD91 to Promote Human Skin Cell Migration against a TGFbeta-Rich Environment during Wound Healing. Molecular and Cellular Biology, May 2008, vol. 28, No. 10, pp. 3344-3358.

(Continued)

*Primary Examiner* — Cherie M Woodward
(74) *Attorney, Agent, or Firm* — McDermott Will & Emery LLP

(57) ABSTRACT

A wound healing composition comprising an amount of heat shock protein effective to promote wound healing and a method thereof to apply the composition. A preferred heat shock protein is either full-length hsp90α or the middle domain plus the charged sequence of hsp90α. The composition is topically applied to skin wounds, covering the outer surface of the wound. The heat shock protein acts by promoting migration of both human epidermal keratinocyte and dermal fibroblasts to the wound in order to close, heal, and remodel the wound.

6 Claims, 3 Drawing Sheets

OTHER PUBLICATIONS

Cheng, C. F. et al. Secretion of Heat Shock Protection-90 (Hsp90) by Normal Cells Under Stress or by Tumor Cells during Invasion: Why? Cancer Therapy, vol. 6, 765-772, 2008, pp. 765-772.

Li, W et al. Extracellular heat shock protein-90α: linking hypoxia to skin cell motility and wound healing. The EMBO Journal (2007) 26, pp. 1221-1233.

Woodley, D. Y. et al. Participation of the lipoprotein receptor LRP1 in hypoxia-HSP90α autocrine signaling to promote keratinocyte migration. Journal of Cell Science 122, (2009), pp. 1495-1498.

Cheng, C.-F. et al. Identification of a Novel Wound Healing Agent That Carries Two Unique Properties for Effectiveness Absent From Conventional Growth Factor Treatments. Unpublished Manuscript submitted 2010. 32 pages.

* cited by examiner

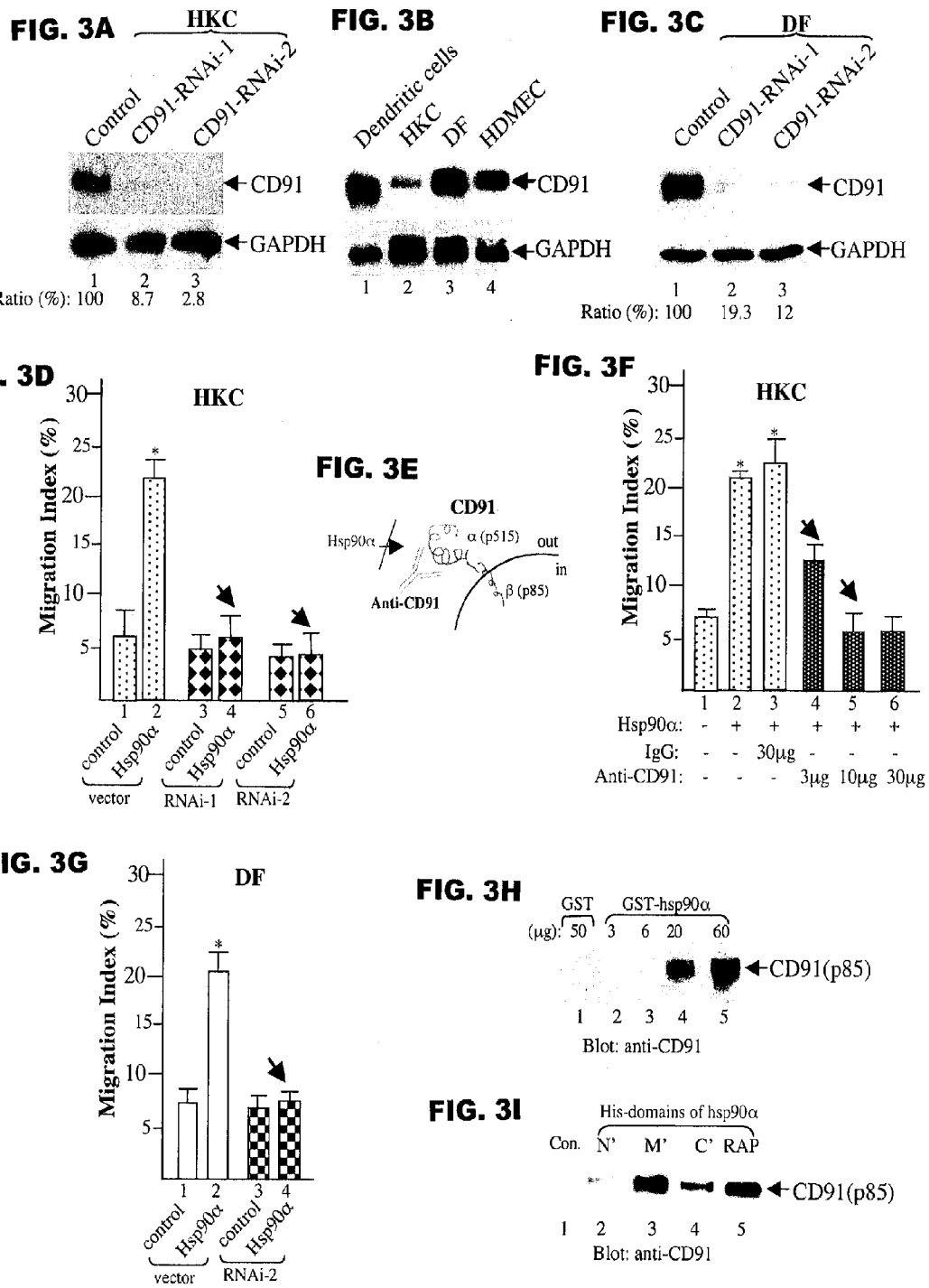

SKIN WOUND HEALING COMPOSITIONS AND METHODS OF USE THEREOF

CROSS REFERENCE TO RELATED APPLICATIONS

This application is a United States national phase application of Patent Cooperation Treaty Application No. PCT/US2008/050520, filed Jan. 8, 2008, which is based upon and claims the benefit of priority from U.S. Provisional U.S. Patent Application 60/879,150, filed on Jan. 8, 2007. The entire contents of both applications are incorporated by reference herein.

STATEMENT REGARDING FEDERALLY SPONSORED RESEARCH

This invention was made with government support under Contract Nos. GM/AR67100-01 and AR46538, awarded by the National Institutes for Health. The U.S. government has certain rights in the invention.

BACKGROUND

1. Field of the Disclosure

This disclosure resides in the field of wound healing compositions and use thereof. Particularly, this disclosure relates to compositions of heat shock proteins (hsp), specifically, the hsp90-alpha (hsp90α) and its derivatives and the topical application of these compositions to human skin wounds to expedite the wound healing process by promoting both epidermal and dermal cell migration.

2. Description of the Related Art

Thirteen percent of Americans are currently 65 years old or older. From 1995 to 2050, this age group is expected to more than double in size. According to the Wound Healing Society, 15% of them suffer from chronic, hard-to-heal wounds. Among the two million people diagnosed yearly with pressure ulcers, 900,000 have non-healing lower extremity ulcers. It is estimated that 18% of patients with diabetes over the age of 65 will have chronic, non-healing foot ulcers. Moreover, 50,000 lower extremity amputations are performed each year due to infected lower leg chronic wounds. The quality of life due to morbidity of non-healing leg ulcers is significantly compromised because of wound odor, infection, and pain. In addition, these issues also lead to social isolation and diminished self-image in patients with chronic skin wounds. Financially, the cost for managing delayed wound healing in the US elderly is estimated at $9 billion per year.

Tremendous effort has been made to develop recombinant growth factors and organotypic skin equivalents for therapy for non-healing wounds. Purchio et al. teaches in U.S. Pat. No. 5,599,788, a method for accelerating skin wound healing with recombinant transforming growth factor β-induced H3 protein by promoting adhesion of human dermal fibroblasts. It was shown that H3 protein promoted adhesion of human dermal fibroblasts to tissue culture plastic.

Akella et al. discloses in U.S. Pat. No. 7,081,240, the use of a protein mixture for treating wounds, wherein the mixture is isolated from bone or produced from recombinant proteins such as bone morphogenetic proteins, transforming growth factors and fibroblast growth factors. However, the overall clinical outcomes of growth factor therapy have been disappointing and few growth factors have ultimately received FDA approval.

Kiss discusses the use of non-growth factor proteins for use in wound healing comprised of human alpha1-antitrypsin, human placental alkaline phosphatase, human transferring and $\alpha_1$-acid glycoprotein. However, this method requires the complicated sequential application of several agents that act at different steps, and also may require adjustment of the compositions according to each treatment.

In chronic wounds, keratinocyte migration is blocked and the wounds remain open, causing patient morbidity and even fatality. During human skin wound healing, a critical rate-limiting step is the initiation of the resident epidermal and dermal cells at the wound edge to migrate into the wound bed. Human keratinocytes (HKCs) laterally migrate across the wound bed from the cut edge to eventually close the wound, the process known as re-epithelialization. The dermal cells, including dermal fibroblasts (DFs) and dermal microvascular endothelial cells (HDMECs), start to move into the wound following the HKC migration, where these cells deposit matrix proteins, contract and remodel the newly closed wound and build new blood vessels. HKC migration is largely driven by TGFα in human serum and is not affected by high concentrations of TGFβ family cytokines co-present in human serum.

In contrast, the presence of TGFβ blocks the dermal cell migration even in the presence of their growth factors, such as PDGF-BB and VEGF. Therefore, while it is understandable why HKC migration jumpstarts ahead of DF and HDMEC migration during wound healing, it has remained as a puzzle how DFs and HDMECs move into the wound bed in the presence of abundant TGFβ.

The heat shock protein (hsp) families include chaperon proteins that are either constitutively expressed, such as the hsp90 family, or stress-induced expression, such as the hsp70 and hsp27 families. Historically, their function is restricted to intracellular proteins, where they interact with and facilitate proper folding and intracellular trafficking of the target proteins to maintain cellular homeostasis and to promote cell survival.

Recently, hsp proteins were found to be actively secreted by cells and carry out important extracellular functions, including stimulation of immunological cytokine production, activation of antigen presenting cells (APCs) and anti-cancer functions. Hypoxia causes hsp90α secretion in both epidermal and dermal cells. The secreted hsp90α in turn promotes migration of these cells. Since hsp proteins lack any signal sequences at the amino terminus, these proteins cannot be secreted via the classical endoplasmic reticulum/Golgi transport pathway. Instead, these proteins are secreted to outside of the cells by a discrete population of nano-vesicles (30-90 nm in diameter), called exosomes. Therefore, the exosome secretion constitutes a potential mode of intercellular communication and opens up new therapeutic and diagnostic strategies. TGFα "pushes" hsp90α out of the human keratinocytes via the exosome pathway, which in turn promotes migration of both the epidermal and dermal cells through the cell surface receptor CD91/LRP-1 ("LRP" meaning LDL receptor-related protein-1).

SUMMARY

This disclosure identifies heat shock protein 90alpha (hsp90α), specifically its middle domain plus the charged sequence, as a novel extracellular pro-motility factor for human epidermal keratinocyte (HKC), dermal fibroblast (DF) and microvascular endothelial cell (HDMEC) migration. Heat shock proteins can help wound healing by enhancing both the re-epithelialization process and recruitments of the dermal cells. The advantages of the use of heat shock protein are: 1) hsp90α can be produced in large quantity and easily purified with less cost; 2) unlike growth factor therapy, the enhancement of wound healing by hsp90α cannot be inhibited by migration-inhibitory factors such as transforming growth factor-beta family cytokines abundantly present in wounds; 3) hsp90α should cause fewer side effects, such as inflammation and simultaneous stimulation of other unrelated cellular responses (e.g., unrelated gene expression, cell proliferation and programmed cell death), which are the common problems associated with previous growth factor and organotypic skin equivalent therapies; and 4) hsp90α can be used as a stand alone treatment, without the complicated process of creating precise mixtures of different proteins for each different treatment.

BRIEF DESCRIPTION OF THE DRAWINGS

FIGS. 3A-3I demonstrate that hsp90α promotes human skin cell migration via the cell surface receptor, CD91/LRP-1 in accordance with another embodiment of the present disclosure.

DETAILED DESCRIPTION OF ILLUSTRATIVE EMBODIMENTS

Figure 1A:
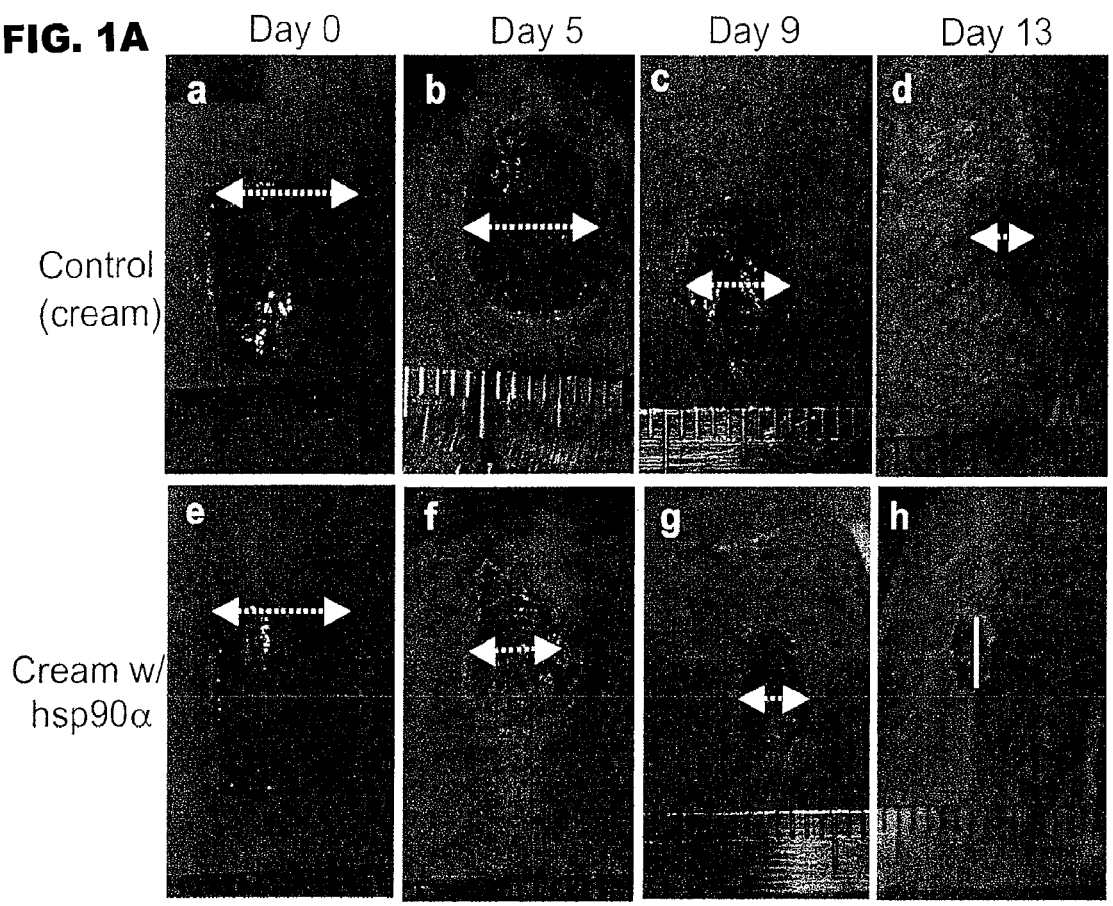
FIGS. 1A and 1B are wound images and a bar graph showing how the topical application of hsp90α enhances wound healing in mice as compared to a control cream in accordance with one preferred embodiment of the present disclosure.

The present disclosure relates to a wound healing composition comprising an amount of hsp90α or the middle domain plus the so-called charged sequence of hsp90α ("Middle domain" may be interchanged with this term) effective to promote wound healing and a pharmaceutical medium to carry the heat shock protein selected from the group consisting of an aqueous solution, suspension, dispersion, salve, ointment, gel, cream, lotion, spray or paste.

In some preferred embodiments, the hsp90α may be of the recombinant form, whereas in other preferred embodiments, the hsp90α may be derived and purified from natural sources.

The present disclosure also relates to a method of healing a skin wound having a step of contacting a first effective amount of a pharmaceutical composition consisting of a heat shock protein to the skin wound. In other preferred embodiments, the method may utilize hsp90α or the middle domain of hsp90α.

In another preferred embodiment, the method of healing a skin wound may also include a pharmaceutical medium to carry the heat shock protein selected from the group consisting of an aqueous solution, suspension, dispersion, salve, ointment, gel, cream, lotion, spray or paste.

The amount of hsp90α or middle domain of hsp90α should be sufficient to effectively promote the wound healing on the skin. In one preferred embodiment, the hsp90α or middle domain of hsp90α is formulated in a concentration of from about 0.1 μg/μl to about 100 μg/μl in said pharmaceutical medium. More preferably, the hsp90α or the middle domain of hsp90α is formulated in a concentration of from about 0.3 μg/μl to about 50 μg/μl in said pharmaceutical medium. Most preferably, the hsp90α or the middle domain of hsp90α is formulated in a concentration of about 1 μg/μl to about 10 μg/μl.

In addition, the amount of the composition applied to the skin in each application may be any amount sufficient to cover the wound such that the heat shock protein may effect wound healing.

The composition may be applied to the wound periodically to further induce wound healing. Generally, the composition may be applied to the wound at least once every about 6 hours to about 72 hours, and preferably once every about 24 hours to about 48 hours. The duration for which the composition may be applied may be sufficient to ensure the healing of the wound. Generally, the composition may be applied for at least 3 days, and more preferably for about 5 days to about 13 days. Those skilled in the art of monitoring the progress of wound healing may evaluate the wound and apply the composition for as long as necessary to ensure that the wound heals.

Not to be bound by theory, it is believed that following skin injury, paracrine- or autocrine-released TGFα stimulates membrane translocation and secretion of pre-existing hsp90α proteins in HKCs. The secreted hsp90α jumpstarts HKC migration, a critical event of re-epithelialization process, by binding to the CD91/LRP-1 receptor on the cell surface. When extracellular hsp90α defuses into and reached certain concentration in the wound bed, it starts to induce migration of DFs and HDMECs from the cut edge into the wound bed even under "hazard" conditions: no ATP and ATPase activity and in presence of general cell motility inhibitors, such as TGFβ family cytokines. Thus, extracellular hsp90α is utilized for skin wound healing.

Figure 1B:
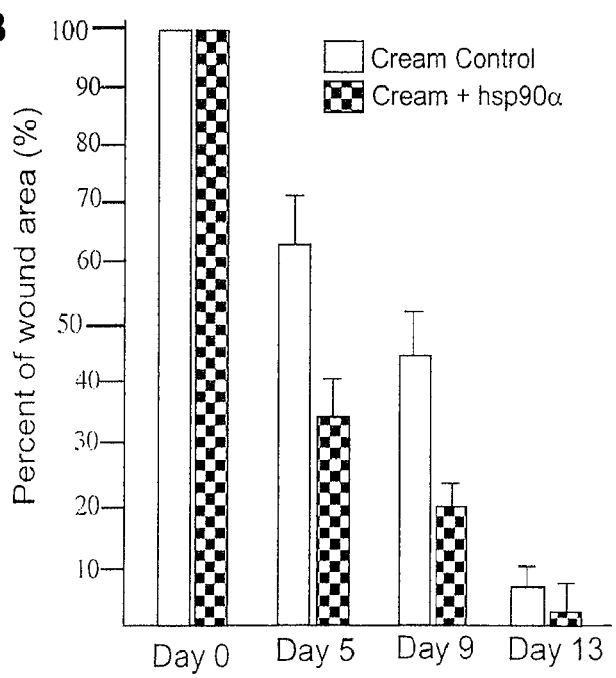

To prove the efficacy of hsp90α or the middle domain of hsp90α as an effective agent for wound healing, human hsp90α cDNA was subcloned into the pET15b bacterium expression system, produced and purified recombinant human hsp90α in milligram quantities. 100 μg hsp90α in 100 μl of 10% Carboxymethylcellulose cream and the cream alone was topically applied to the 1 cm×1 cm wound on the back of nude mice daily for 5 days, and wounds were analyzed every two days. Selected wound images of a representative experiment are shown in FIG. 1A. It can be seen that hsp90α significantly accelerated closure of the wounds on day 5, day 9 and day 13 as compared to the cream control (see, FIG. 1A, panel f vs. panel b and panel g vs. panel c). Quantitation of the data from four independent experiments is shown in FIG. 1B, which indicates an overall 30% improvement of the wound healing.

Figure 2A:
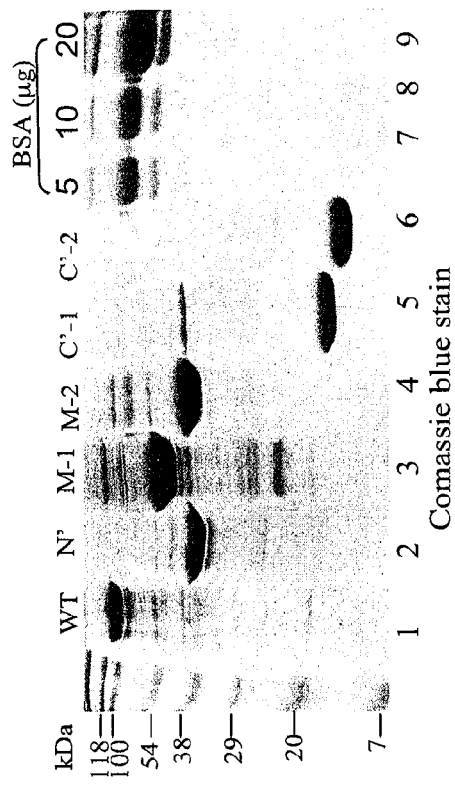
FIGS. 2A and 2B show gel electrophoresis study indicating the molecular weight of the hsp90α and its domains and the migration index of these domains in accordance with another embodiment of the present disclosure.

As is shown in FIG. 2A, hsp90α is composed of an N'-terminal domain, a charged sequence, a middle domain and a C'-terminal domain. The middle and C'-terminal domains are exposed at the surface of hsp90α protein. To demonstrate which of these domains carries out the pro-motility function of extracellular hsp90α, the individual domains were constructed, expressed in bacteria as His-tagged proteins and purified by FPLC. Equal molarities of the proteins were then tested for pro-motility effects on HKCs.

Five distinct domains (N', M-1. M-2, C'-1 and C'-2) of hsp90α were constructed as above. After Ni-NTA column purification, each of the domain proteins was concentrated in Centricon YM-50 or YM-10 to the volume of ~4 ml depending on the size of the domains. These domains were then purified by FPLC in a Superdex 75 HiLoad gel filtration column (GE healthcare, Piscataway, N.J.) and followed by concentrated in Centricon YM-50 or YM-10 to the final concentration of 1 mg/ml.

The purified wild type and the indicated fragments of human hsp90α proteins were: FIG. 2A verified in an SDS-PAGE and Comassie blue staining and FIG. 2B subjected to colloidal gold migration assays (0.1 μM each), in comparison to control serum-free medium. Only the migration indices were shown. n=3.

Figure 2B:
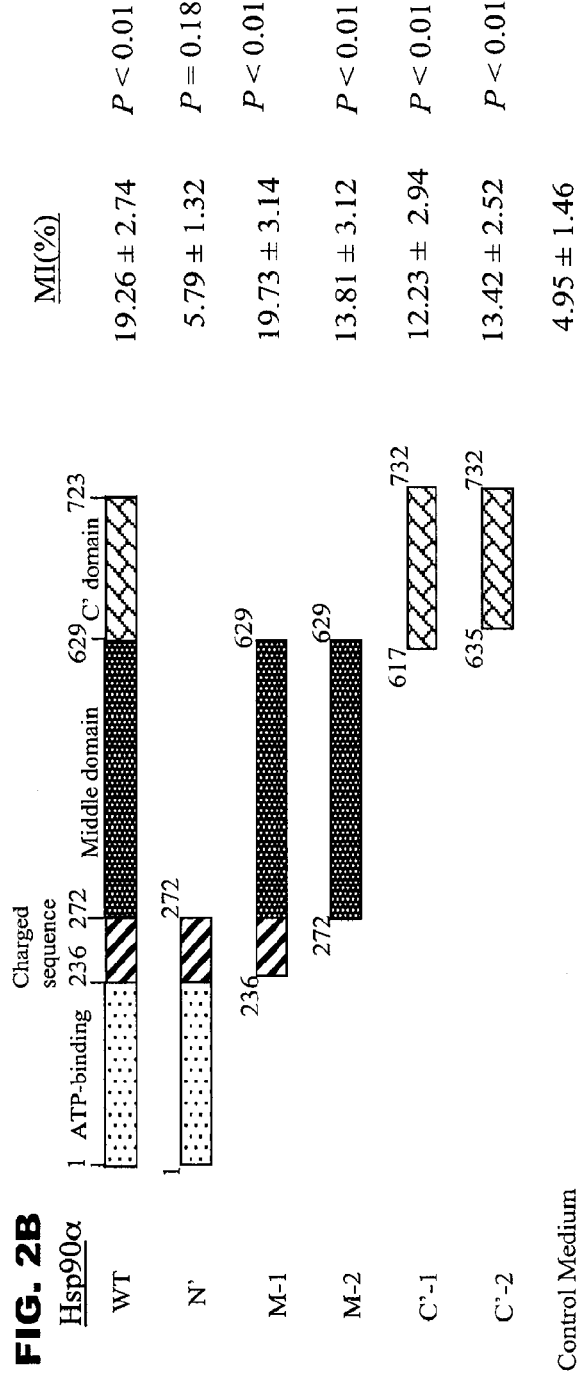

As can be seen in FIG. 2B, the full-length (WT) hsp90α showed a remarkable pro-motility activity, in comparison to the control medium. The middle domain plus the charged sequence (M-1) show a similar degree of the activity as the WT hsp90α. However, the middle domain lacking the charged sequence showed a significantly decreased activity (M-2), although the charged sequence plus the entire N'-terminal domain (N') showed no stimulating activity. The two C'-terminal domains (C'-1 and C'-2, made to ensure the results) both showed a moderate pro-motility activity. Therefore, hsp90α promotes HKC migration mainly through its middle and the carboxyl domains, consistent with their surface location in hsp90α. Accordingly, a composition comprising the middle domain of hsp90α would exhibit similar wound healing properties as that of a composition comprising hsp90α alone.

As is shown in FIGS. 3A-3I, CD91/LRP is the cell surface receptor that mediates the function of hsp90α.

FIG. 3A shows CD91-RNAi-1 and CD91-RNAi-2 down-regulated almost completely the endogenous CD91 protein (lane 2 and 3 vs. lane 1). Lysates of HKCs infected with lentivirus carrying either a control siRNA (LacZ-siRNA) or two siRNAs against CD91 (CD91-RNAi-1 and CD91-RNAi-2) were analyzed by Western blot with an anti-CD91 antibody. When these cells were subjected to migration assays, as shown in FIG. 3D, hsp90α strongly stimulated HKC migration (bar 2). The effects of down-regulation of CD91 by two distinct siRNAs on HKC migration in response to hsp90α (10 μg/ml) were analyzed in colloidal gold migration assays. Here, down-regulation of CD91 completely blocked HKC cell migration in response to hsp90α (bars 4 and 6 vs. bar 2). In FIG. 3D, bars with * are statistically significant over serum-free controls, n=4, p<0.03.

Second, a monoclonal neutralizing antibody was used to block the cell surface CD91, as schematically shown in FIG. 3E. FIG. 3F indicates how hsp90α strongly stimulated HKC migration (bars 2 vs. bar 1), while addition of a control IgG showed little effect (bar 3). For the data shown in FIG. 3F, HKCs on collagen in colloidal gold migration assays were pre-incubated with increasing concentrations of an anti-CD91 neutralizing antibody for 30 min (and continued presence throughout the assays) or control IgG prior to addition of hsp90α. However, addition of even 3 μg/ml of anti-CD91 antibodies completely blocked hsp90α-induced HKC migration in a dose-dependent manner (bars 4-6 vs. bar 2).

In comparison to HKCs, DFs and HDMECs are not only CD91-positive but express relatively even higher CD91, shown by Western blots. (FIG. 3B, lanes 3 and 4 vs. lane 2). Dendritic cells were included as a positive control (lane 1). When CD91 in DFs was down-regulated by siRNA (FIG. 3C) and tested in migration assays, also analyzed by Western blot with an anti-CD91 antibody, hsp90α was no longer able to stimulate migration of DFs (FIG. 3G, bar 4). The effects of RNAi down-regulation of CD91 on DF migration in response to hsp90α (10 μg/ml) were analyzed in colloidal gold migration assays. In FIG. 3G, bars with * are statistically significant over serum-free controls, n=3, p<0.05. In contrast, hsp90α still stimulated migration of the vector alone-infected DFs (bar 2). This example indicates the importance of CD91 in hsp90α signaling using other human skin cell types is thereby confirmed.

In FIG. 3H, lysates of HKCs were incubated with indicated amounts of GST-hsp90α fusion proteins or GST alone on beads and beads-bound proteins were dissociated and analyzed by Western blot with an anti-CD91 antibody. As shown in FIG. 3H, using GST-hsp90α pull-down assays, GST alone was unable to bind any CD91 from the lysates of HKCs (lane 1). However, GST-hsp90α pulled down CD91 in a dose-dependent manner (lanes 2-5). Using His-tagged domains of hsp90α on beads, as shown in FIG. 3I, lysates of HKCs were incubated with 20 μg each of three His-tagged domains of hsp90α on Ni+ beads. The bound proteins were analyzed by Western blot with an anti-CD91 antibody. n=3, p<0.05. FIG. 3I shows that, among the N'-terminal ATP binding and ATPase domain, the middle domain and the C'-terminal domain, the middle domain of hsp90α (lane 3) bound strongest to CD91 than the C'-terminal and the N'-terminal domain (lanes 4 and 2). Receptor-associated protein (RAP) (lane 5), a known CD91-binding protein, and empty beads (lane 1) were included as a positive and negative controls, respectively. Taken together, these findings indicate that CD91 is a receptor for secreted hsp90α, whose real extracellular function might be to promote migration of all CD91+ skin cell types during wound healing.

EXAMPLE

In the example below, the following conditions or methods were utilized.

To obtain hsp90α, human hsp90α cDNA is cloned into the bacterium protein expression system, pET15b (Novagen) and the protein is synthesized inside bacteria as a His-tagged fusion protein. After breaking the bacteria, the His-tagged hsp90α can be easily purified by a Ni affinity column. The His tag can then be cleaved by thrombin digestion and the His tag-free hsp90α is further purified by FPLC chromatography using the Superdex 200 seizing column (Pharmacia).

The pharmaceutical 100 μl of 10% carboxymethylcellulose cream (Sterile) is mixed in and the 1 cm×1 cm wound on the back of a nude mouse is topically covered. Following this treatment, the wound is covered with a few antibiotics and bandi and the bandi are fixed by rolling the mouse with coban. The hsp90α mix is then added every day for up to five days and the wound is analyzed every two days.

To prepare mice for topical treatment of hsp90α, 1.0-cm×1.0-cm full-thickness excision wounds were made by lifting the skin with forceps and removing full thickness skin with a pair of scissors on the mid-back of 8 to 10 week old mice. The wounds were topically covered by 100 μl 10% carboxymethylcellulose either without (as a control) or with 100 μg recombinant hsp90α protein. The wound area was then covered with Band-Aid and Coban, a self-adherent wrap, to prevent desiccation. Fresh recombinant hsp90α proteins were applied to the wounds daily up to 5 days. To measure the wound area, standardized digital photographs were taken of the wounds at 0, 5, 9, 13 days post-wounding and the open wound areas were determined with an image analyzer (AlphaEase FC version 4.1.0, Alpha Innotech Corporation). Percentage of wound area was defined by comparing areas of healing wounds to those of the original wounds. The Student T test was used for the statistical analysis. All animal studies were conducted using protocols approved by the University of Southern California Institutional Animal Use Committee.

The following example is offered for purposes of illustration and are not intended to limit the scope of the invention.

A 1.0-cm² (1 cm×1 cm) square full-thickness excision wound was made on the mid-back of 8 to 10 week old athymic nude mice and the pharmaceutical composition of human recombinant hsp90α was applied topically daily for 5 days (n=10 mice per group). (A) Representative day 0, 5, 9, and 13 wounds are shown. Wound sizes were significantly reduced in mice topically treated with the cream containing hsp90α (lower panels), but not cream alone (upper panels). (B) Mean±SD wound size measurements at day 0, 5, 9, and 13 post-wounding (n=10 mice for each group).

The foregoing is offered primarily for illustrative purposes. The present disclosure is not limited to the above described embodiments, and various variations and modifications may be possible without departing from the scope of the present invention.

The invention claimed is:

1. A wound healing composition comprising:
an isolated polypeptide fragment comprising the middle domain and the charged sequence of hsp90α, wherein the isolated polypeptide fragment does not comprise the N-terminal ATP-binding domain or the C-terminal C' domains of hsp90α, in a therapeutically effective amount to promote wound healing in a patient in need thereof; and
a pharmaceutical medium to carry the polypeptide fragment.

2. The wound healing composition according to claim 1, wherein the amount of polypeptide fragment is from about 0.1 μg/μl to about 100 μg/μl in said pharmaceutical medium.

3. The wound healing composition according to claim 1, wherein the amount of polypeptide fragment is from about 0.3 μg/μl to about 50 μg/μl in said pharmaceutical medium.

4. The wound healing composition according to claim 1, wherein the polypeptide fragment contains 394 amino acid units.

5. The wound healing composition according to claim 1, wherein the polypeptide fragment is from about 38 Kdaltons to about 54 Kdaltons.

6. The wound healing composition according to claim 1, wherein the pharmaceutical medium is at least one selected from the group consisting of: an aqueous solution, suspension, dispersion, salve, ointment, gel, cream, lotion, spray or paste.

* * * * *